United States Patent [19]

Jansons et al.

[11] Patent Number: 4,826,947
[45] Date of Patent: May 2, 1989

[54] PREPARATION OF POLY(ARYLENE ETHER KETONES)

[75] Inventors: Viktors Jansons, Los Gatos; John B. Mazzanti, Belmont; Stephen Moore, Redwood City, all of Calif.

[73] Assignee: Raychem Corporation, Menlo Park, Calif.

[21] Appl. No.: 72,187

[22] Filed: Jul. 9, 1987

[51] Int. Cl.[4] .......................... C08G 8/02; C08G 14/00
[52] U.S. Cl. .................................... 528/125; 528/126; 528/127; 528/128; 528/174; 528/175
[58] Field of Search ................ 528/125, 126, 127, 174, 528/175, 128

[56] References Cited

U.S. PATENT DOCUMENTS

| | | | |
|---|---|---|---|
| 3,065,205 | 5/1962 | Bonner | 528/180 |
| 3,441,538 | 7/1969 | Marks | 528/86 |
| 3,516,966 | 8/1970 | Berr | 528/194 |
| 3,767,620 | 12/1973 | Angelo | 525/419 |
| 4,645,819 | 5/1987 | Sterzel | 528/125 |
| 4,687,833 | 8/1987 | Clendinning et al. | 528/176 |

FOREIGN PATENT DOCUMENTS

971227 9/1964 United Kingdom .
1086021 10/1964 United Kingdom .
WO8403891 3/1984 W.I.P.O.

Primary Examiner—John Kight
Assistant Examiner—M. L. Moore
Attorney, Agent, or Firm—Yuan Chao; Edith A. Rice; Herbert G. Burkard

[57] ABSTRACT

A method of preparing a poly(arylene ether ketone) having a repeat unit

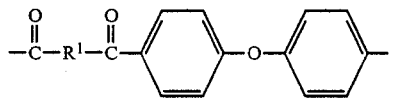

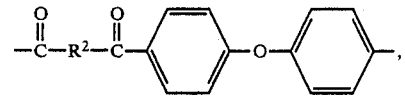

comprising polymerizing a monomer system comprising
(I) a monomer of the formula

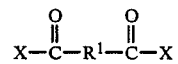

and
(II) a monomer of the formula

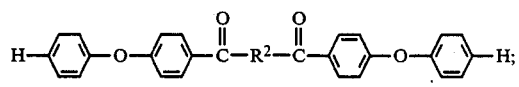

wherein
$R^1$ is p-phenylene, m-phenylene, or 4,4'-biphenylene;
$R^2$ is p-phenylene, m-phenylene, biphenylene, or naphthylidene; and
X is a group displaceable under Friedel-Crafts polymerization conditions;
in a polymerization medium comprising
(a) a Lewis base present in an amount between about 0.05 and about 2 equivalents per equivalent of acid halide groups present in the monomer system and
(b) a Lewis acid present in an amount of at least one equivalent per equivalent of carbonyl groups present, plus an equivalent per equivalent of Lewis base present, plus an amount effective to act as a catalyst for the polymerization.

31 Claims, 6 Drawing Sheets

FIG_1

FIG_2

FIG_3

FIG_4

FIG_6

PREPARATION OF POLY(ARYLENE ETHER KETONES)

BACKGROUND OF THE INVENTION

This invention relates to a method of preparing poly(arylene ether ketones) and to novel poly(arylene ether ketones).

Poly(arylene ether ketones), particularly those wherein a substantial fraction or all of the arylene groups are p-phenylene, possess many desirable properties, for example, high temperature stability, mechanical strength, and resistance towards common solvents. Among these, the poly(arylene ether ketone) having the repeat unit , where . denotes has been the focus of considerable attention. Bonner, in U.S. Pat. No. 3,065,205; Goodman et al., in GB No. 971,227; Jones, in GB No. 1,086,021; and Marks, in U.S. Pat. No. 3,441,538; each disclose the preparation of such a polymer by the Friedel-Crafts polymerization of tere- and/or isophthaloyl chloride with diphenyl ether. While such a synthetic approach is attractive because of the ready availability of the monomers, resulting polymer appears to have defects which limit its thermal stability and/or its melt processability and utility. Berr, in U.S. Pat. No. 3,516,966 reported that the all-para polymer was not melt-processable and degraded under melt processing conditions.

Angelo, in U.S. Pat. No. 3,767,620, addressed the problem of poor melt stability of certain poly(arylene ether ketones), stating: "[P]olyketones prepared from diphenyl ether and terephthaloyl and isophthaloyl halides in the presence of Friedel Crafts catalysts invariably contain 9-phenylenexanthydrol end-groups, generally in the amount of about 0.6 to 1.0 % by weight. These 9-phenylenexanthydrol end-groups have been found to be a major factor in the poor melt stability of this type of polyketone." Angelo proposed treating the polymer with a reducing agent, converting the 9-phenylenexanthydrol groups to 9-phenylenexanthene groups. He found that 9-phenylenexanthydrol groups could be detected by UV-VIS spectroscopy thermally stable reduced polymer having an absorbance at 4550 521 of less than 0.18 and as-made, thermally unstable polymer having an absorbance of at least 0.20 and generally greater than about 0.25. While reduction may improve melt stability, the 9-phenylenexanthene groups, possessing tertiary hydrogen atoms, are themselves susceptible to air oxidation at elevated temperatures. Additionally, the method of Angelo requires a separate post-polymerization treatment step, which may be impractical on a large scale.

Sterzel, in U.S. Pat. No. 4,645,819, discloses that heat-stable poly(arylene ether ketone) may be prepared by polymerization of terephthaloyl chloride or fluoride and diphenyl ether in a homogeneous phase, for example anhydrous hydrogen fluoride with boron trifluoride catalyst. However, the boron trifluoride-hydrogen fluoride system requires special techniques and equipment, making this process difficult to practice on a commercial scale.

We have unexpectedly discovered that high molecular weight, melt-processable poly(arylene ether ketones) can be prepared by replacing the diphenyl ether in the monomer system with other monomers having two hydrogens activated towards displacement in a Friedel-Crafts polymerization. In particular, our invention enables the preparation of poly(arylene ether ketones) having the repeat unit without using diphenyl ether as a monomer and without using hydrogen fluoride-boron trifluoride as the polymerization medium, thus avoiding the above-described problems.

SUMMARY OF THE INVENTION

This invention provides a method for preparing a poly(arylene ether ketone) having a repeat unit comprising polymerizing a monomer system comprising (I) a monomer of the formula and
(II) a monomer of the formula wherein
R' is p-phenylene, m-phenylene, or 4,4,'-biphenylene;
$R^2$ is p-phenylene, m-phenylene, biphenylene, or naphthylidene; and
X is a group displaceable under Friedel-Crafts polymerization conditions; in a polymerization medium comprising (a) a Lewis base present in an amount between about 0.05 and about 2 equivalents per equivalent of acid halide groups present in the monomer system and
(b) a Lewis acid present in an amount of at least one equivalent per equivalent of carbonyl groups present, plus an equivalent per equivalent of Lewis base present, plus an amount effective to act as a catalyst for the polymerization.

DETAILED DESCRIPTION OF THE INVENTION

Poly(arylene ether ketones) of this invention have a repeat unit wherein $R^1$ and $R^2$ are as hereinabove defined. In preferred embodiments, $R^1$ and $R^2$ are independently m-phenylene or p-phenylene, in which case the above formula can be simplified to:

In the method of our invention, a monomer other than diphenyl ether is the precursor of the subunit and a different reaction medium is employed, thereby avoiding the aforementioned disadvantages of the prior art. The monomer system of our invention comprises
(I) a monomer of the formula and
(II) a monomer of the formula wherein $R^1$ is p-phenylene, m-phenylene, or 4,4,-biphenylene; $R^2$ is p-phenylene, m-phenylene, biphenylene, or naphthylidene; and X is a group displaceable under Friedel-Crafts polymerization conditions.

Where $R^2$ is biphenylene, it is preferably 3,3'- or 4,4,'-biphenylene. Where $R^2$ is naphthylidene, it is preferably 2,6,3,6- or 1,4-naphthylidene. X is preferably halide, especially chloride, or $OR^3$, where $R^3$ is lower alkyl, for example isopropyl, ethyl, or methyl.

Monomer (I) is preferably [1,1'-biphenyl]-4,4'-dicarbonyl dichloride, terephthaloyl chloride, or isophthaloyl chloride. Monomer (II) is preferably 1,4-bis(4-phenoxybenzoyl)benzene or 1,3-bis(4-phenoxybenzoyl)benzene.

Within the scope of this invention combinations of more than one monomer (I) may be polymerized with a monomer (II), or vice-versa, or even two or more monomers (I) may be copolymerized with two or more monomers (II). For example, terephthaloyl chloride and [1,1,-biphenyl]-4,4,-dicarbonyl dichloride may be copolymerized with 1,4-bis(4-phenoxybenzoyl)benzene to produce a copoly(arylene ether ketone) having a first repeat unit and a second repeat unit The total molar amount of monomer (I) should substantially equal to the total molar amount of monomer (II), if high molecular weight polymer is desired. A slight stoichiometric imbalance in the monomers may be mployed, for the purpose of molecular weight control or capping, as is well known in the art and is discussed in more detail hereinbelow. For example, the amount of monomer (I) may be in slight excess over the amount of monomer (II), or vice-versa.

In addition to the monomers (I) and (II), small amounts of other monomers may be copolymerized with them, provided that they do not affect the essential character of the copolymers of this invention and stoichiometric adjustments, if necessary, are made for their presence, so as not to prevent the achievement of high molecular weights. Examples of suitable additional monomers include: 4,4,'-diphenoxydiphenyl sulfone, naphthalene-1,4-dicarbonyl dichloride, naphthalene-2,6-dicarbonyl dichloride, naphthalene-3,6-dicarbonyl dichloride, 1,4-diphenoxybenzene, 1,4-diphenoxybenzophenone, diphenyl ether-4,4'-dicarbonyl dichloride, p-phenoxybenzoyl chloride, and the like.

The polymerization medium of this invention comprises (a) a Lewis base present in an amount between about 0.05 and about 2 equivalents per equivalent of acid halide groups present in the monomer system and (b) a Lewis acid present in an amount of at least one equivalent per equivalent of carbonyl groups present, plus an equivalent per equivalent of Lewis base present, plus an amount effective to act as a catalyst for the polymerization.

The use of a Lewis acid and Lewis base in a Friedel-Crafts polymerization is described by Jansons et al. in published PCT application WO No. 84/0389, the disclosure of which is incorporated herein by reference.

The term "Lewis acid" is used herein to refer to a substance which can accept an unshared electron pair from another molecule. Lewis acids which may be used in the practice of this invention include, for example, aluminum trichloride, aluminum tribromide, antimony pentachloride, antimony pentafluoride, indium trichloride, gallium trichloride, boron trichloride, boron trifluoride, zinc chloride, ferric chloride, stannic chloride, titanium tetrachloride, and molybdenum pentachloride. Aluminum trichloride, boron trichloride, aluminum tribromide, titanium tetrachloride, antimony pentachloride, ferric chloride, gallium trichloride, and molybdenum pentachloride are preferred. Aluminum trichloride is particularly preferred.

The Lewis base is preferably selected from the group consisting of amides, amines, esters, ethers, thioethers, ketones, nitriles, nitro compounds, phosphines, phosphine oxides, phosphoramides, sulfides, sulfones, sulfonamides, sulfoxides, and halide salts.

Suitable Lewis bases include acetone, benzophenone, cyclohexanone, methyl acetate, ethylene carbonate, N-methylformamide, acetamide, N,N-dimethylacetamide, N-methylpyrrolidone, urea, tetramethylurea, N-acetylmorpholine, dimethylsulfoxide, diphenyl sulfone, N,N-dimethylmethanesulfonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulfide, trimethylamine, N,N,N',N'-tetramethylethylenediamine, N,N-dimethyldodecylamine, imidazole, pyridine, quinoline, isoquinoline, benzimidazole, 2,2'-bipyridine, o-phenanthroline, 4-dimethylaminopyridine, and the like. In addition to covalent organic compounds, suitable Lewis bases include inorganic salts which can form complexes with Lewis acids, for example, chlorides, such as trimethylammonium chloride, tetramethylammonium chloride, sodium chloride or lithium chloride, perchlorates, trifluoromethanesulfonates, and the like.

Preferred Lewis bases are selected from the group consisting of N-methylformamide, N,N-dimethylformamide, N,N-dimethylacetamide, 1-methyl-2-pyrrolidone, tetramethylenesulfone also known as sulfolane), n-butyronitrile, dimethylsulfide, imidazole, acetone, benzophenone, trimethylamine, trimethylamine hydrochloride, tetramethylammonium chloride, pyridine-N-oxide, 1-ethylpyridinium chloride, lithium chloride, lithium bromide, sodium chloride, sodium bromide, and mixtures thereof.

Particularly preferred Lewis bases are N,N-dimethylformamide, N,N-dimethylacetamide, tetramethylene sulfone, dimethyl sulfone, and lithium chloride.

The Lewis base is used in an amount between 0.05 equivalent per equivalent of acid halide groups present, more preferably 0.5 equivalent per equivalent of acid halide groups present, and 4 equivalents per equivalent of acid halide groups present in the monomers system. Amounts greater than 4 equivalents could be employed, if desired. However, no additional controlling effect is usually achieved by adding larger amounts. Thus, it is preferred to use no more than about 4 equivalents and generally no more than about 2 equivalents.

The temperature at which the reaction is conducted is not critical and may be from about $-70°$ C. to about $+150°$ C., or even higher. It is preferred to start the reaction at lower temperatures, for example at $-50°$ to about $-10$ ° C., particularly if the monomer system contains highly reactive monomers. After polymerization has commenced, the temperature may be raised if desired, for example, to increase the rate of reaction. It is generally preferred to carry out the reaction at temperatures in the range of between $-30°$ C. and $+25°$ C. (room temperature).

A nonprotic—also known as aprotic—diluent may also be employed, if desired. Advantageously, the diluent should dissolve the Lewis acid/Lewis base complex and the resulting polymer/Lewis acid complex, but this is not an essential requirement for the diluent. The diluent should also be be relatively inert towards Friedel-Crafts reactions. The diluent is preferably somewhat polar as measured by its dielectric constant and solubility parameter. Preferably the dielectric constant of the diluent is at least about 2.5 at 24° C., and more preferably in the range of from about 4.0 to about 25 at 24° C. The Hildebrand solubility parameter of the diluent is preferably at least about 7.2 $[cal/cm^3]^{\frac{1}{2}}$ and is preferably in the range of from about 9.2 to about 15 $[cal/cm^3]^{\frac{1}{2}}$. Preferred diluents include methylene chloride, carbon disulfide, o-dichlorobenzene, 1,2,4-trichlorobenzene, o-difluorobenzene, 1,2-dichloroethane, 1,1,2,2-tetrachloroethane, and tetrachloroethylene.

The diluent is used in an amount from 0 to about 95% by weight, based on the weight of the total reaction mixture. As is known in polymerizations of this type, the reactions can be run neat, that is without the presence of a diluent.

The polymers of this invention are unexpectedly free of defect generally found in comparable polymers made using diphenyl ether as a monomer. The presence or absence of such defects is readily detected measuring the absorbancy index ($A_s$) of the polymer, with the wavelength of measurement being indicated parenthetically in nanometers (nm). Thus $A_s(474)$ denotes an $A_s$ measured at 474 nm. Generally, $A_s(474)$ is reported to facilitate comparison of different experiments. $A_s$ is calculated according to the following formula:

$A_s = [\log (1/T)]/bc$ where b is the light path length in centimeters, c is the sample concentration in g/mL, and T is the transmittance at the wavelength in question. The solvent is trifluoroacetic acid-methylene chloride, 50:50 volume/volume. The sample is typically prepared by dissolving 150 mg polymer in 10 mL of solvent. The polymers of this invention have low $A_s$'s, by which is meant an $A_s(474)$ less than 50, preferably less than 25, most preferably less than 15.

The polymers of this invention are preferably high molecular weight polymers. By "high molecular weight," it is meant a polymer having an inherent viscosity greater than about 0.6 dL/g. Preferably the polymer has an inherent viscosity in the range of about 0.6 to about 2.0 dL/g. Polymers having an inherent viscosity below about 0.6 are generally not useful because they have poor mechanical properties, such as low tensile strength and elongation, while polymers having an inherent viscosity above about 2.0 are very difficult to melt process. Throughout this application, inherent viscosity refers to the mean inherent viscosity determined according to the method of Sorenson et al., "Preparative Methods of Polymer Chemistry," 2nd ed., (Interscience 1968), at page 44 (0.1 g polymer dissolved in 100 mL of concentrated sulfuric acid at 25° C.).

If desired, the molecular weight of the polymer, the degree of branching, and the amount of gelation may be controlled by use of, for example, capping agents as described by Dahl in U.S. Pat. No. 4,247,682, the disclosure of which is incorporated herein by reference. The molecular weight of the polymer may also be controlled by employing a slight excess of one of the monomers.

Capping agents, when employed, are added to the polymerization reaction medium to cap the polymer on at least one end of the polymer chain. This terminates continued growth of the chain and controls the resulting molecular weight of the polymer, as shown by the inherent viscosity of the polymer. Judicious use of the capping agents results in a polymer within a selected narrow molecular weight range, decreased gel formation during polymerization, and decreased branching of the polymer chains and increases melt stability. Both nucleophilic and electrophilic capping agents may be used to cap the polymer at each end of the chain.

Preferred nucleophilic capping agents are 4-chlorobiphenyl, 4-phenoxybenzophenone, 4-(p-phenoxyphenoxy)benzophenone, biphenyl, 4-benzenesulfonylphenyl phenyl ether, and the like.

Typical electrophilic capping agents are compounds of the formula $Ar$—$CO$—$E$ or $Ar$—$SO_2$—$E$ wherein Ar is phenyl, 3-chlorophenyl, 4-chlorophenyl, 4-cyanophenyl, 4-methylphenyl, napthyl, biphenyl, or an aromatic group substituted with an electron withdrawing substituent and E is halogen or other leaving group, preferably chloride. Preferred electrophilic capping agents include benzoyl chloride, benzenesulfonyl chloride, and the like.

In the preparation of the copolymers of this invention by a Friedel-Crafts polymerization, a Lewis acid is employed. As a result, the polymer contains Lewis acid complexed to the carbonyl groups of the polymer. For many polymerizations, the Lewis acid is complexed to substantially all the carbonyl groups in the polymer. As is well known with polymers of this type, the catalyst residue must be removed, i.e., the Lewis acid must be decomplexed from the polymer and removed. A method for removing the catalyst residue is described by Dahl in U.S. Pat. No. 4,237,884, the disclosure of which is incorporated herein by reference.

Decomplexation may be accomplished by treating the polymerization reaction mixture with a decomplexing base after completion of polymerization. The base can be added to the reaction medium or the reaction medium can be added to the base. The decomplexing base must be at least as basic towards the Lewis acid as the basic groups on the polymer chain. Such decomplexation should be effected before the isolation of the polymer from the reaction mixture.

The amount of decomplexing base used should be in excess of the total amount of bound (complexed) and unbound Lewis acid present in the reaction mixture and is preferably twice the total amount of Lewis acid. Typical decomplexing bases which can be used include water, dilute aqueous hydrochloric acid, methanol, ethanol, acetone, N,N-dimethylformamide, N,N-dimethylacetamide, pyridine, dimethyl ether, diethyl ether, tetrahydrofuran, trimethylamine, trimethylamine hydrochloride, dimethyl sulfide, tetramethylene sulfone, benzophenone, tetramethylammonium chloride, isopropanol, and the like. The decomplexed polymer can then be recovered by conventional techniques such as separating the polymer by filtration; adding a nonsolvent for the polymer which is a solvent for or miscible with the Lewis acid/Lewis base complex and the Lewis acid; spraying the reaction medium into a nonsolvent for the polymer; or evaporating the volatiles from the reaction medium and then washing with an appropriate solvent to remove any remaining base/catalyst complex and diluent from the polymer.

In the recovery of the polymer from the reaction mixture, the reaction mixture may be liquefied, if desired, by the method described by Reamey in U.S. Pat. No. 4,665,151, the disclosure of which is incorporated herein by reference.

EXAMPLE 1

A 500 mL round bottom flask equipped with a reflux condenser, nitrogen inlet, and magnetic stirrer was charged with chlorobenzene (150 mL), thionyl chloride (44.1 mL, 0.605 mol), and N,N-dimethylformamide (1 mL). 4,4'-Biphenyldicarboxylic acid (24.2 g, 0.102 mol) was added, with stirring. The reaction mixture was heated at reflux for about 4 hrs, at the end of which period the reaction mixture was a bright orange homogeneous solution. Excess thionyl chloride was distilled from the reaction under reduced pressure (water aspirator). The warm residual solution was poured into a mixture of hexanes (300 mL), yielding a pale yellow precipitate.

The product was isolated by filtration, washed with hexanes, and dried in vacuo at 100° C. overnight. Two sublimations (165° C./0.05 mm Hg) afforded polymerization grade [1,1'-biphenyl]-4,4'-dicarbonyl dichloride, mp 185.5°–187° C.

EXAMPLE 2

1,4-Bis(4-phenoxybenzoyl)benzene was prepared according to the following procedure.

A 1 L, 3-neck round bottom flask equipped with a nitrogen inlet, thermometer, and magnetic stirring bar was charged with methylene chloride (250 mL), dimethylsulfone (28.233 g), and aluminum trichloride (102.72 g). The flask was immersed in a cooling bath maintained at between −30° and −35° C. While maintaining this temperature, diphenyl ether (95.06 mL, 0.600 mol) was added dropwise through an addition funnel over a period of 30 min. After completion of the addition of the diphenyl ether, terephthaloyl chloride (40.605 g, 0.200 mol) was added slowly via a solid addition funnel. The reaction was allowed to proceed for 30 min.

The reaction mixture was poured into cold methanol (−30° C.) with vigorous stirring. The methanol slurry was allowed to warm to room temperature, then heated to reflux and filtered while hot to afford pasty white crude 1,4-bis(4-phenoxybenzoyl)benzene. This was washed with methanol and dried overnight in a vacuum oven at 100° C.

The 1,4-bis(4-phenoxybenzoyl)benzene was recrystallized from chlorobenzene (after dissolving the crude product at reflux and filtration through Celite). It was isolated as colorless flakes, mp 212°–214° C. Its $A_s(474)$ was 2.8 before recrystallization and 2.2 afterwards.

EXAMPLE 3

1,3-Bis(4-phenoxybenzoyl)benzene was prepared by the procedure of EXAMPLE 2, except as noted below.

The terephthaloyl chloride was replaced by an equivalent amount of isophthaloyl chloride and the reaction period was 1 hr at −30° C. followed by 2 hrs at 0° C.

The reaction mixture was poured into cold methanol (2 L). The methanol slurry was allowed to warm up to room temperature and then heated to reflux. The warm slurry was filtered. The filter cake was triturated with fresh methanol (3 L). The white crude 1,3-bis(4-phenoxybenzoyl)benzene was dried in vacuo overnight at 60° C. Recrystallization from isopropanol afforded colorless product, mp 117°–119° C. and $A_s(514)$ 1.9.

EXAMPLE 4

[1,1,-Biphenyl]-4,4'-dicarbonyl dichloride was polymerized with 1,3-bis(4-phenoxybenzoyl)benzene by the following procedure.

A 100 mL resin kettle, fitted with a mechanical stirrer and a nitrogen inlet, was charged with methylene chloride (24 mL). The temperature was lowered to −30° C. Aluminum trichloride (133.7 mmol) and dimethyl sulfone (30 mmol) were added, and the contents of the kettle were stirred at a moderate rate. When the exotherm had subsided, the [1,1'-biphenyl]-4,4''-dicarbonyl dichloride (20.00 mmol) was quantitatively transferred to the kettle, with a methylene chloride rinse to ensure quantitative transfer. The resulting slurry was stirred for a few minutes. Next, 1,3-bis(4-phenoxybenzoyl)benzene (20.36 mmol) and benzoyl chloride (0.72 mmol, capping agent) were added, again with a methylene chloride rinse. The benzoyl chloride, along with the stoichiometric excess of 1,3-bis(4-phenoxybenzoyl)benzene served to double cap the polymer. The total amount of methylene chloride used, including the rinses, was 32 mL.

The reaction was allowed to warm to ambient temperature (ca. 20° C.) and was stirred for about 40 min. The reaction was allowed to continue, for a total reaction time of about 24 hr.

At the completion of the reaction, the gelled reaction mixture was broken up manually and decomplexed in 0.15% aqueous hydrochloric acid (500 mL). The resulting polymer was isolated by filtration and washed with tap water (3×500 mL). The polymer was then digested at reflux overnight in 0.15% aqueous hydrochloric acid, isolated by filtration, and washed with tap water (3×500 mL). Next, the polymer was heated at reflux for 1 hr in 0.15% aqueous ammonium hydroxide (500 mL), isolated by filtration, and washed with tap water (3×500 mL). Finally, the polymer was dried in vacuo overnight at 165° C.

The resulting polymer had a repeat unit

Figure 1:
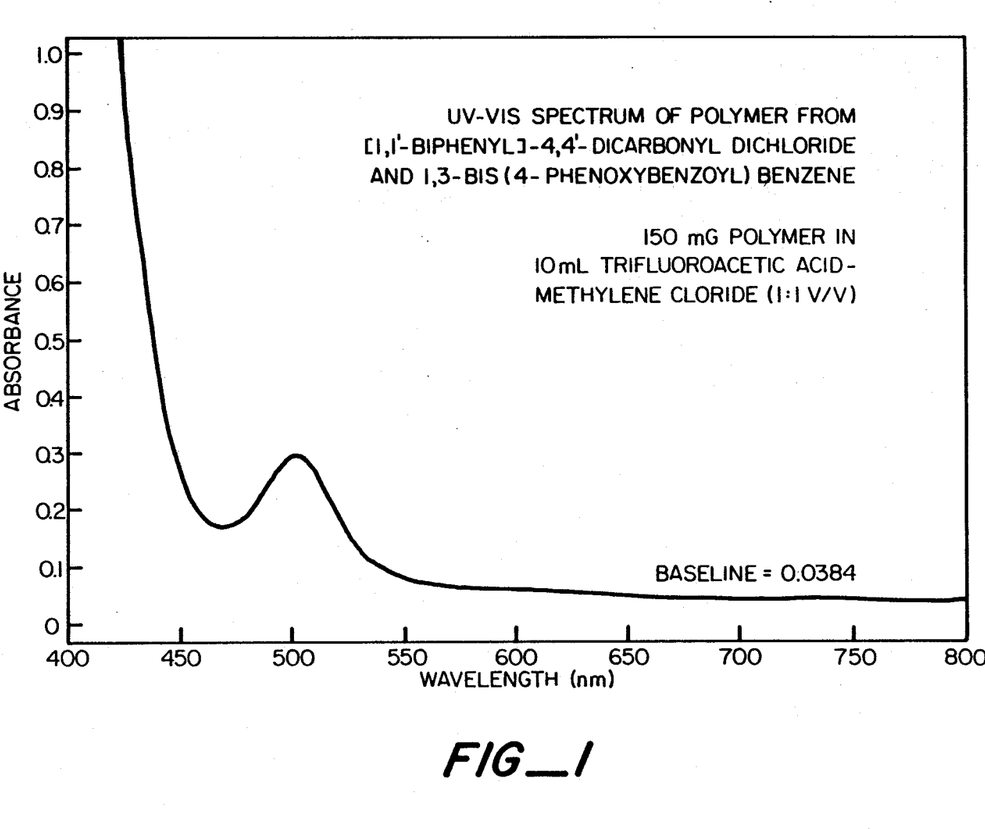
FIG. 1 is the UV-Vis spectrum of the polymer from the polymerization of [1,1'-biphenyl]-4,4,-dicarbonyl dichloride and 1,3-bis(4-phenoxybenzoyl)benzene.

Its inherent viscosity was 0.53 dL/g. Its thermal transitions were Tg 163° C. and Tm 356°, 387° C. (multiple transitions). Its $A_s(474)$ was 9.3 and its $A_s(502)$ was 17.2. Its UV-Vis spectrum is given in FIG. 1.

EXAMPLE 5

[1,1'-Biphenyl]-4,4'-dicarbonyl dichloride, terepthaloyl chloride, and 1,4-bis(4-phenoxybenzoyl)benzene were copolymerized following the procedure of EXAMPLE 4, except that (a) the amount of dimethyl sulfone used was 40 mmol, (b) the amount of aluminum trichloride used was 151.8 mmol, and (c) the amount of monomers and capping agent were as provided in Table I.

The resulting copolymers had a first repeat unit and a second repeat unit

Figure 2:
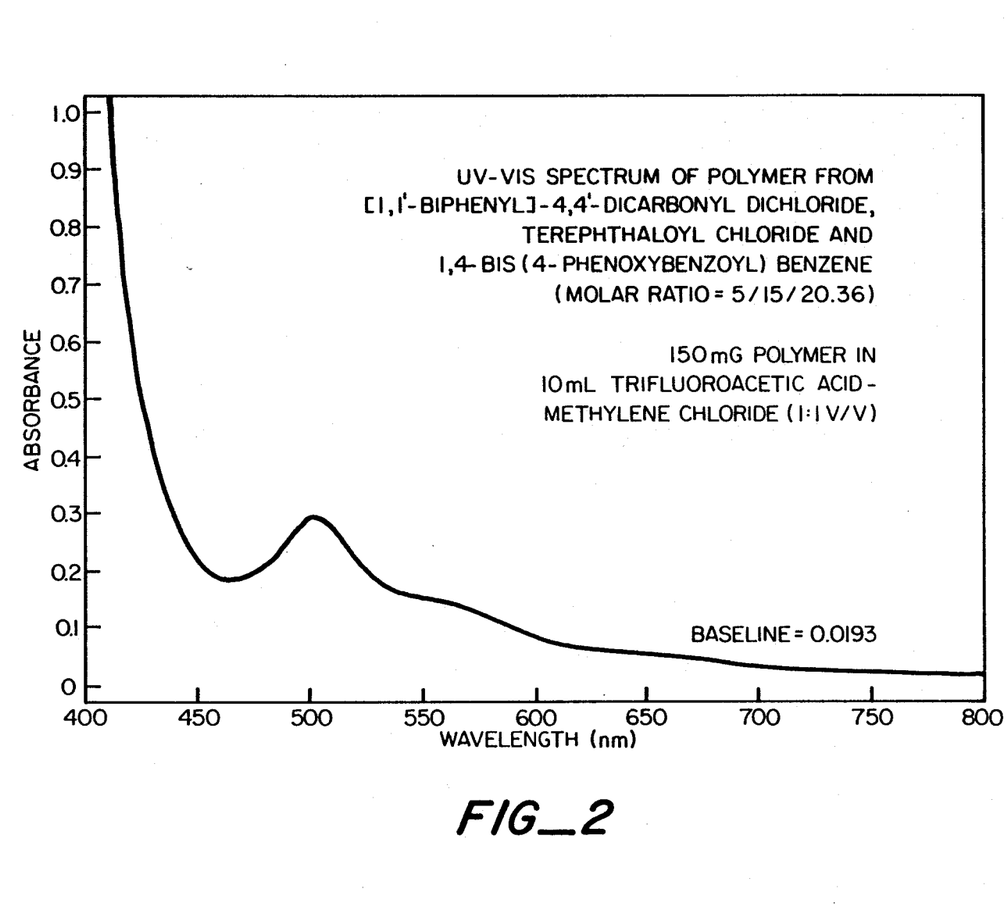
FIGS. 2 through 4 are the UV-Vis spectra of the polymers from the polymerization of [1,1'-biphenyl]-4,4'-dicarbonyl dichloride, terephthaloyl chloride, and 1,4-bis(4-phenoxybenzoyl)benzene, the [1,1,-biphenyl]-4,4,-dicarbonyl dichloride/terephthaloyl chloride molar ratio being 5/15, 10/10, and 15/5, respectively.
Figure 3:
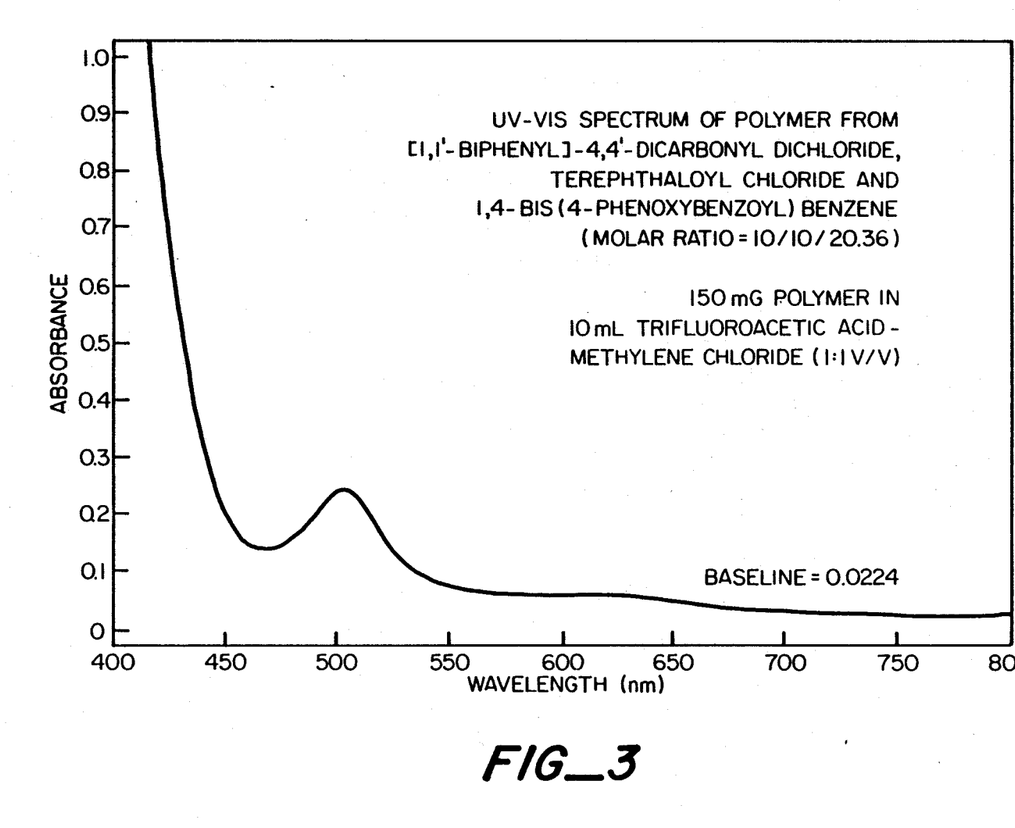
Figure 4:
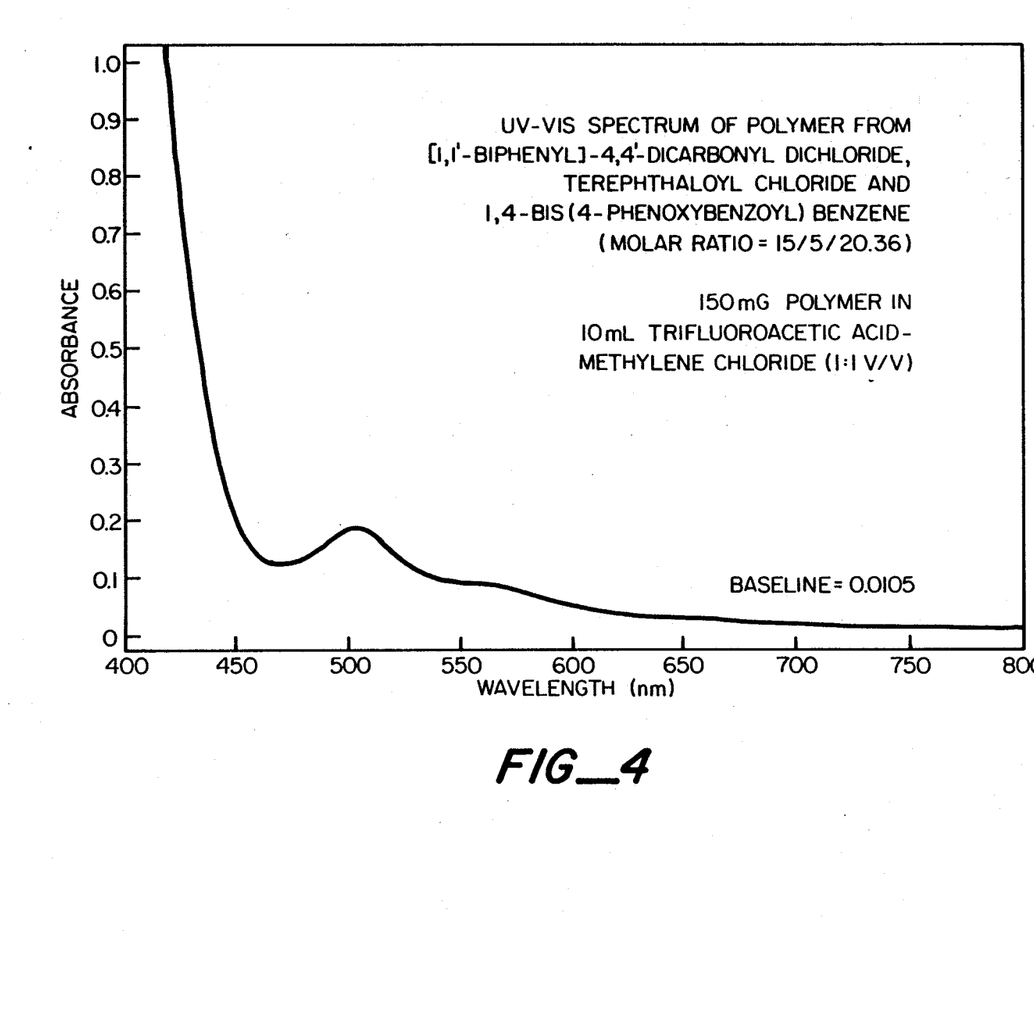

The molar ratio of first repeat units to second repeat unit varied according to the molar ratio of monomers used in each run. The inherent viscosity, Tg, Tm, and $A_s(474)$ of the copolymers obtained are given in Table I. The UV-Vis spectra for the copolymers are given in FIGS. 2 through 4, corresponding to [1,1'-biphenyl]-4,4'-dicarbonyl dichloride/terephthaloyl chloride molar ratios of 5/15, 10/10, and 155, respectively.

TABLE I

| Monomers & capping agt. (mmol) | | | | Inh. Vis. (dL/g) | Tg (°C.) | Tm (°C.) | $A_s$(474) |
|---|---|---|---|---|---|---|---|
| (a) | (b) | (c) | (d) | | | | |
| 5.0 | 15.0 | 20.36 | 0.72 | 0.78 | 168 | 376 | 12.0 |
| 10.0 | 10.0 | 20.36 | 0.72 | 0.87 | 170 | 340* | 9.3 |
| 15.0 | 5.0 | 20.36 | 0.72 | 0.62 | 174 | 417 | 8.0 |

(a) = [1,1'-biphenyl]-4,4'-dicarbonyl dichloride
(b) = terephthaloyl chloride
(c) = 1,4-bis(4-phenoxybenzoyl)benzene
(d) = benzoyl chloride
*Additional melting endotherms at 260 and 393° C.

EXAMPLE 6

Terephthaloyl chloride and 1,4-bis(4-phenoxybenzoyl)-benzene were polymerized as follows.

A 500 mL resin kettle equipped with mechanical stirrer and nitrogen inlet was charged with methylene chloride (61.9 mL) and aluminum trichloride (35.47 g, 0.266 mol). The flask was immersed in a cooling bath at −30° C. To the cold suspension was added dimethyl sulfone (5.646 g, 0.06 mol). The mixture was again cooled at −30° C. Next were added, in order, terephthaloyl chloride (8.121 g, 0.04 mol) and 1,4-bis(4-phenoxybenzoyl)benzene (19.198 g, 0.0408 mol, $A_s$(474) 2.7). The resulting mixture was maintained at −30° C. for 3 min. The temperature of the cooling bath was then increased to +20° C. Reaction was allowed to proceed at this temperature for 6.5 hr.

The gelled reaction mixture was worked up by decomplexing in N,N-dimethylformamide (DMF) in a Waring blender. The polymer was isolated by filtration and digested in DMF for 16 hr. It was then washed with water, digested in 0.015% hydrochloric acid for 6 hr at ca. 80° C., filtered, washed with water, digested in 0.15% ammonium hydroxide for 1.5 hr at ca. 80° C., and dried at 200° C. in vacuo for 16 hr.

The polymer obtained had a repeat unit which can be rewritten in simplified form as Its inherent viscosity was 0.93 dL/g, its Tg was 180° C., and its Tm 386°–389° C. Its $A_s$(452) was 6.8, and its $A_s$(474) was 5.5.

The tensile properties of filament extruded from this polymer are summarized in Table II.

TABLE II

| | Temperature (°C.) | | | |
|---|---|---|---|---|
| | 25 | 150 | 200 | 250 |
| Tensile Strength (psi) | 10,100 | 9,400 | 9,400 | 8,900 |
| Elongation (%) | 28 | 183 | 215 | 170 |
| Young's Modulus | 330,000 | 238,000 | 74,000 | 45,000 |

TABLE II-continued

| | Temperature (°C.) | | | |
|---|---|---|---|---|
| | 25 | 150 | 200 | 250 |
| (psi) | | | | |

EXAMPLE 7

This is a comparative example not within the scope of the invention, in which terephthaloyl chloride and diphenyl ether are copolymerized.

An 100 mL resin kettle, fitted with a mechanical stirrer and nitrogen inlet, was charged with anhydrous aluminum chloride (10.00 g, 135 mmol) and methylene chloride (20 mL). The resulting suspension was cooled to −30° C. with a cooling bath, whereupon dimethylsulfone (3.529 g, 37.5 mmol) was added. When the exothermic reaction had subsided, terephthaloyl chloride (5.076 g, 25.0 mmol) and diphenyl ether (4.25 g, 25.0 mmol) was added. The containers from which the monomers were transferred were rinsed with methylene chloride (10 mL) to ensure quantitative transfer. Once addition of the monomers was complete, the external cooling bath was removed and the reaction mixture was allowed to warm up to ambient temperature.

After 2.5 hr, the reaction mixture was transferred to a 1 at. Waring blender containing 0.15% aqueous hydrochloric acid (300 mL). After blending, the polymer was isolated by filtration and washed with water. The polymer was then digested in 15% aqueous hydrochloric acid (400 mL, 16 hr., ca. 80° C.) and isolated and washed as before. Then, the polymer was digested in 0.15% ammonium hydroxide (400 mL, 1 hr, reflux) and isolated and washed as before. The polymer was then dried in vacuo at 180° C./0.2 mm Hg for 16 hr.

The resulting polymer had a repeat unit

Its inherent viscosity was 0.37 dL/g and its $A_s$(474) was 310 and its $A_s$(450) was 371.

EXAMPLE 8

Isophthaloyl chloride and 1,3-bis(4-phenoxybenzoyl)benzene were polymerized as follows.

A 100 mL resin kettle equipped with a mechanical stirrer and nitrogen inlet was charged with methylene chloride (20 mL) and the temperature lowered to −30° C. via a cooling bath. Aluminum trichloride (133.73 mmol) and dimethyl sulfone (30.00 mmol) were added and the contents of the kettle were stirred at a moderate rate. The isophthaloyl chloride (20.00 mmol) was next added. After a few minutes, 1,3-bis(4-phenoxybenzoyl)-benzene (20.36 mmol) and benzoyl chloride (capping agent, 0.72 mmol) were added, with a methylene chloride (11 mL) rinse to ensure quantitative transfer.

The reaction mixture was allowed to warm to room temperature. Shortly thereafter the reaction mixture became homgeneous, and within 1.5 hr had gelled. Stirring was stopped and reaction was allowed to proceed for another 6 hr, for a total reaction time of 7.5 hr.

The gelled reaction mixture was broken up by hand stirring and decomplexed in deionized water (500 mL). The resulting white polymer was isolated by filtration, washed with tap water (3×500 mL), digested at reflux overnight in 0.15% aqueous hydrochloric acid, filtered, washed with tap water (3×500 mL), and dried in vacuo at 160° C.

The resulting polymer had a repeat unit

[chemical structure]

which can be rewritten in simplified form as

[chemical structure]

Figure 5:
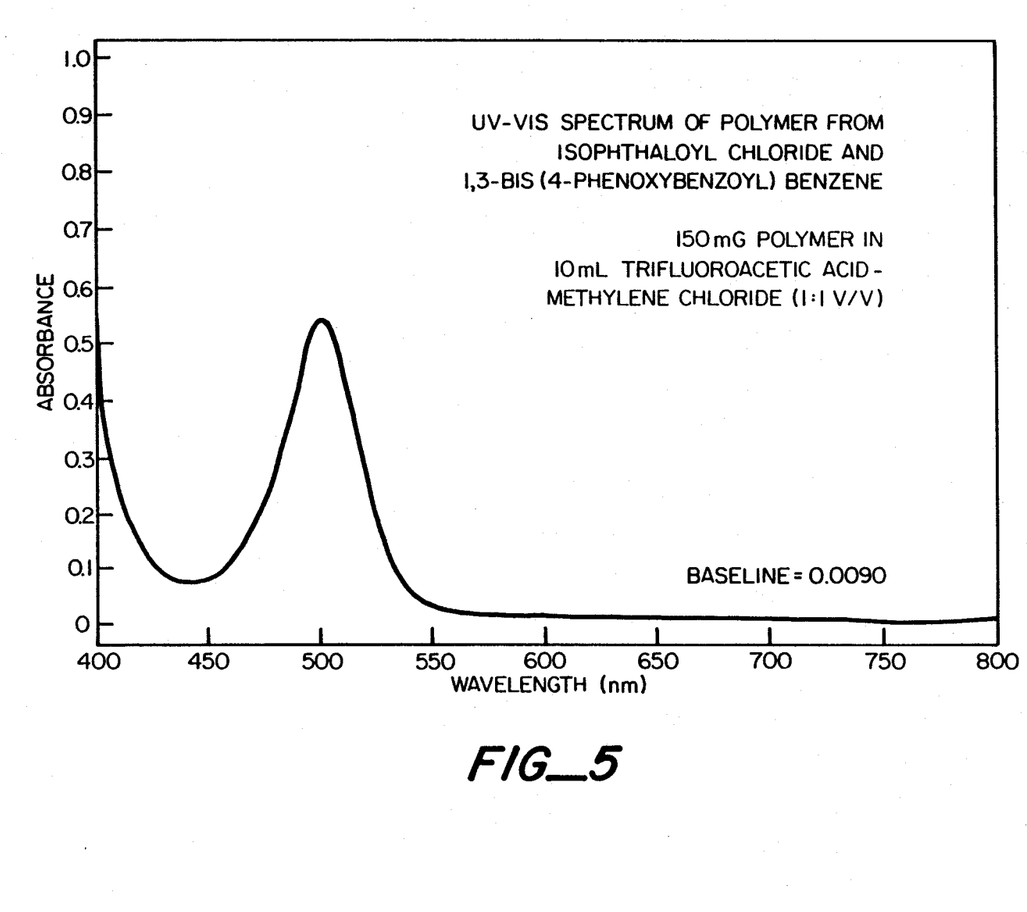
FIG. 5 is the UV-Vis spectrum of the polymer from the polymerization of isophthaloyl chloride and 1,3-bis(4-phenoxybenzoyl)benzene.

Its inherent viscosity was 0.81 dL/g and its $A_s(474)$ was 14. Its UV-Vis spectrum is provided in FIG. 5.

EXAMPLE 9

This is a comparative example not within the scope of the invention, in which isophthaloyl chloride and diphenyl ether are copolymerized.

A 120 mL reaction vessel equipped with nitrogen inlet, magnetic stirring bar, and cooling bath was used. N,N-Dimethylacetamide (DMAC, 0.90 g, 10.30 mmol, Aldrich Gold Label) was added gradually to aluminum trichloride (2.74 g, 20.59 mmol, Witco #0099) in methylene chloride (2.0 mL), while maintaining the temperature at about 24° C. with a cooling bath. Some of the aluminum trichloride went into solution, but some of it remained undissolved. This mixture was then added gradually to a solution of diphenyl ether (1.7526 g, 10.30 mmol, Aldrich Gold Label) and isophthaloyl chloride (2.0905 g, 10.30 mmol, sublimed) in methylene chloride (8.0 mL) cooled at about −40° C. The mixture was allowed to warm up to about −30° C. over 1 hour, at which point additional aluminum trichloride (5.49 g) and lithium chloride (0.449 g, 10.30 mmol) was added. The reaction mixture was then allowed to warm up to 24° C. over about 2.5 hr.

After allowing reaction to proceed overnight at about 24° C., the gelled reaction mixture was worked up by blending with ice/water, filtering, washing with water and then methanol, and soaking in methanol for about 2.5 days. Next, the polymer was boiled in water for 3 hr, filtered, blended in water, washed in water then methanol, and soaked in methanol overnight. After filtration and drying in vacuo at 120° C., off-white polymer was obtained. It had a repeat unit

[chemical structure]

Its inherent viscosity was 0.95 and its $A_s(452)$ was 297.

EXAMPLE 10

EXAMPLE 8 was repeated, except that the isophthaloyl chloride was replaced with an equivalent amount of terephthaloyl chloride and the total reaction time was 6.5 hr.

The resulting polymer had a repeat unit

[chemical structure]

Figure 6:
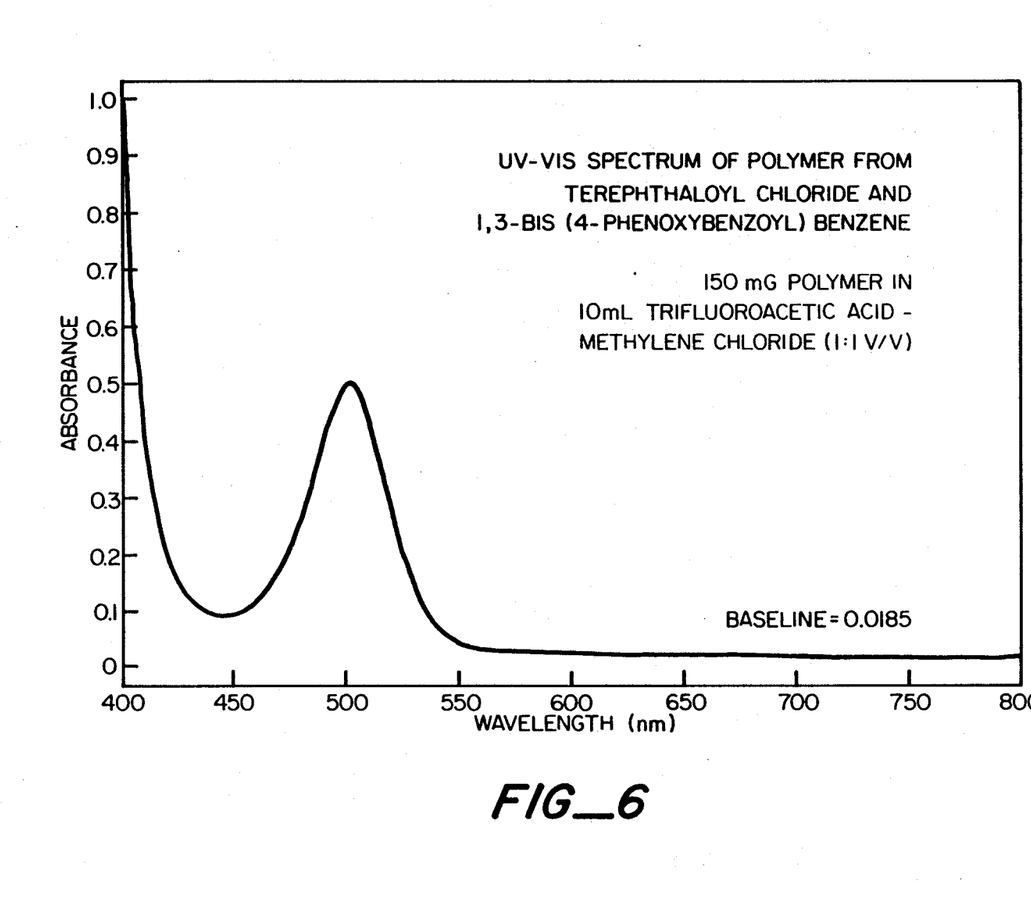
FIG. 6 is the UV-Vis spectrum of the polymer from the polymerization of terephthaloyl chloride and 1,3-bis(4-phenoxybenzoyl)benzene.

Its inherent viscosity was 1.10 dL/g and its $A_s(474)$ was 12. Its UV-Vis spectrum is provided in FIG. 6.

A polymer with the same repeat unit was prepared by polymerizing isophthaloyl chloride with 1,4-bis(4-phenoxybenzoyl)benzene. It had $A_s(452)$ 18.5 and $A_s(474)$ 13.2.

EXAMPLE 11

Tere- and isophthaloyl chloride and 1,4-bis(4-phenoxybenzoyl)benzene were polymerized as follows.

A 500 mL resin kettle equipped with magnetic stirrer, cooling bath, and nitrogen inlet was charged with 1,4-bis(4-phenoxybenzoyl)benzene (25.79 g, 54.8 mmol), terephthaloyl chloride (7.67 g, 37.8 mmol), isophthaloyl chloride (3.32 g, 16.35 mmol) and benzoyl chloride (capping agent, 0.154 g, 1.09 mmol) and 1,2-dichloroethane (130 mL). The mixture was stirred at 24° C. for 15 min, then cooled to −35° C. Aluminum trichloride (67.53 g, 506.45 mmol) was added gradually over 30 min, followed by lithium chloride (6.90 g, 162.35 mmol). The mixture was allowed to warm to 0° C. gradually (over 1¼ hr), at the end of which period a red-orange gel had formed. The mixture was then warmed up to 24° C. over 1 hr and held there for another 2 hr.

The gelled reaction mixture was broken up manually and decomplexed in dilute hydrochloric acid/ice, blended, filtered, washed with dilute hydrochloric acid, and digested overnight with more dilute hydrochloric acid. The polymer was then filtered, washed with water then methanol and digested overnight in methanol. The polymer was next filtered, washed with water, and stirred in 0.5% pentasodium tripolyphosphate for 2 hr. Filtration, washing to neutrality with water, and vacuum drying at 165° C. yielded white polymer fluff (31.70 g, 97.5% yield).

The polymer had the repeat units and

Its inherent viscosity was 1.25 dL/g and its $A_s(452)$ was 6.9. A slab made by pressing at 400° C. for 30 min had inherent viscosity 1.24 dL/g.

The polymer fluff was compacted in a twin-screw compacting extruder and extruded in a 3/8 inch miniextruder with temperature zones of 352°, 397° and 405° C. (die), yielding smooth, light colored crystallized (opaque) extrudate of inherent viscosity 1.24 dL/g.

We claim:

1. A method for preparing a poly(arylene ether ketone) having a repeat unit comprising polymerizing a monomer system comprising (I) a monomer of the formula and (II) a monomer of the formula wherein $R^1$ is p-phenylene, m-phenylene, or 4,4''-bi-phenylene;

$R^2$ is p-phenylene, m-phenylene, biphenylene, or naphthylidene; and

X is a group displaceable under Friedel-Crafts polymerization conditions;

in a polymerization medium comprising (a) a Lewis base present in an amount between about 0.05 and about 4 equivalents per equivalent of acid halide groups present in the monomer system and (b) a Lewis acid present in an amount of at least one equivalent per equivalent of carbonyl groups present, plus an equivalent per equivalent of Lewis base present, plus an amount effective to act as a catalyst for the polymerization.

2. A method in accordance with claim 1, wherein the Lewis base is present in an amount between about 0.5 equivalent per equivalent of acid halide groups present and about 2 equivalents per equivalent of acid halide groups present.

3. A method in accordance with claim 1, wherein the Lewis acid is selected from the group consisting of aluminum trichloride, boron trichloride, aluminum tribromide, titanium tetrachloride, antimony pentachloride, ferric chloride, gallium trichloride, and molybdenum pentachloride.

4. A method in accordance with claim 1, wherein the Lewis acid is aluminum trichloride.

5. A method in accordance with claim 1, wherein the Lewis base is selected from the group consisting of amides, amines, esters, ethers, thioethers, ketones, nitriles, nitro compounds, phosphines, phosphine oxides, phosphoramides, sulfides, sulfones, sulfonamides, sulfoxides, and halide salts.

6. A method in accordance with claim 1, wherein the Lewis base is selected from the group consisting of acetone, benzophenone, cyclohexanone, methyl acetate, ethylene carbonate, N-methylformamide, acetamide, N,N-dimethylacetamide, N-methylpyrrolidone, urea, tetramethylurea, N-acetylmorpholine, dimethylsulfoxide, diphenyl sulfone, N,N-dimethylmethanesulfonamide, phosphoryl chloride, phenylphosphonyl chloride, pyridine-N-oxide, triphenylphosphine oxide, trioctylphosphine oxide, nitropropane, nitrobenzene, benzonitrile, n-butyronitrile, methyl ether, tetrahydrofuran, dimethyl sulfide, trimethylamine, N,N,N',N'-tetramethylethylenediamine, N,N-dimethyldodecylamine, imidazole, pyridine, quinoline, isoquinoline, benzimidazole, 2,2'-bipyridine, o-phenanthroline, and 4-dimethylaminopyridine.

7. A method in accordance with claim 1, wherein the Lewis base is selected from the group consisting of N-methylformamide, N,N-dimethylformamide, N,N-dimethylacetamide, 1-methyl-2-pyrrolidone, tetramethylenesulfone, n-butyronitrile, dimethylsulfide, imidazole, acetone, benzophenone, trimethylamine, trimethylamine hydrochloride, tetramethylammonium chloride, pyridine-N-oxide, 1-ethylpyridinium chloride, lithium chloride, lithium bromide, sodium chloride, sodium bromide, and mixtures thereof.

8. A method in accordance with claim 1, wherein the Lewis base is selected from the group consisting of N,N-dimethylformamide, N,N-dimethylacetamide, tetramethylene sulfone, dimethyl sulfone, and lithium chloride.

9. A method in accordance with claim 1, wherein the Lewis acid is aluminum trichloride and the Lewis base is selected from the group consisting of N,N-dimethylformamide, N,N-dimethylacetamide, tetramethylene sulfone, dimethyl sulfone, and lithium chloride.

10. A method in accordance with claim 9, wherein the Lewis base is N,N-dimethylformamide.

11. A method in accordance with claim 9, wherein the Lewis base is N,N-dimethylacetamide.

12. A method in accordance with claim 9, wherein the Lewis base is tetramethylene sulfone.

13. A method in accordance with claim 9, wherein the Lewis base is dimethyl sulfone.

14. A method in accordance with claim 9, wherein the Lewis base is lithium chloride.

15. A method in accordance with claim 1, wherein the polymerization is carried out in the presence of a non-protic diluent.

16. A method in accordance with claim 15, wherein the diluent has a dielectric constant of at least about 2.5 at 24° C.

17. A method in accordance with claim 15, wherein the diluent has a dielectric constant in the range of from about 4.0 to about 25 at 24° C.

18. A method in accordance with claim 15, wherein the diluent is selected from the group consisting of methylene chloride, carbon disulfide, o-dichlorobenzene, 1,2,4-trichlorobenzene, o-difluorobenzene, 1,2-dichloroethane, 1,2,3,4-tetrachloroethane, and tetrachloroethylene.

19. A method in accordance with claim 1, wherein monomer (I) is selected from the group consisting of terephthaloyl chloride, isophthaloyl chloride, and [1,1'biphenyl]-4,4'-dicarbonyl dichloride and monomer (II) is selected from the group consisting of 1,4-bis(4-phenoxybenzoyl)benzene and 1,3-bis(4-phenoxy- benzoyl)benzene.

20. A method in accordance with claim 19, wherein monomer (I) is terephthaloyl chloride and monomer (II) is 1,4-bis(4-phenoxybenzoyl)benzene.

21. A method in accordance with claim 19, wherein monomer (I) is terephthaloyl chloride and monomer (II) is 1,3-bis(4-phenoxybenzoyl)benzene.

22. A method in accordance with claim 19, wherein monomer (I) is isophthaloyl chloride and monomer (II) is 1,4-bis(4-phenoxybenzoyl)benzene.

23. A method in accordance with claim 19, wherein monomer (I) isophthaloyl chloride and monomer (II) is 1,3-bis(4-phenoxybenzoyl)benzene.

24. A method in accordance with claim 19, wherein monomer (I) is [1,1'-biphenyl]-4,4'-dicarbonyl dichloride and monomer (II) is 1,4-bis(4-phenoxybenzoyl)benzene.

25. A method in accordance with claim 19, wherein monomer (I) is 1,1'-biphenyl-4,4'-dicarbonyl dichloride and monomer (II) is 1,3-bis(4-phenoxybenzoyl)benzene.

26. A method in accordance with claim 1, wherein a capping agent is added to the reaction medium.

27. A method in accordance with claim 26, wherein both a nucleophilic and an electrophilic capping agent are added to the reaction medium.

28. A method in accordance with claim 27, wherein the nucleophilic capping agent is selected from the group consisting of 4-chlorobiphenyl, 4-phenoxybenzophenone, biphenyl, 4-(4-phenoxyphenoxy)benzophenone, and 4-benzenesulfonylphenyl phenyl ether.

29. A method in accordance with claim 27, wherein the electrophilic capping agent is selected from the group consisting of benzoyl chloride and benzenesulfonyl chloride.

30. A poly(arylene ether ketone) having the repeat unit

31. A copoly(arylene ether ketone) having a first repeat unit and a second repeat unit

* * * * *